United States Patent [19]
Bailey

[11] Patent Number: 5,186,625
[45] Date of Patent: Feb. 16, 1993

[54] CONTROL FOR DENTAL AIR-POLISHER

[75] Inventor: Ronald L. Bailey, Harvester, Mo.

[73] Assignee: Young Dental Manufacturing Company, Earth City, Mo.

[21] Appl. No.: 619,037

[22] Filed: Nov. 28, 1990

[51] Int. Cl.[5] .......................... A61C 3/02; A61C 1/10; A61C 1/02; A61G 17/02

[52] U.S. Cl. ........................................ 433/88; 433/80; 433/84; 433/98; 433/28

[58] Field of Search .................. 433/80, 84, 85, 88, 433/89, 98, 101, 77, 79, 28; 51/428, 438

[56] References Cited

U.S. PATENT DOCUMENTS

| | | | |
|---|---|---|---|
| 2,245,036 | 6/1941 | Henschel | 433/84 |
| 3,858,358 | 1/1975 | Stachowiak et al. | 51/8 |
| 3,863,028 | 2/1975 | Vit | 128/66 |
| 3,882,638 | 5/1975 | Black | 51/12 |
| 3,991,473 | 11/1976 | Morgan | 433/28 |
| 4,482,322 | 11/1984 | Hain et al. | 433/88 |
| 4,487,582 | 12/1984 | Varrin | 433/88 |
| 4,494,932 | 1/1985 | Rzewinski | 433/88 |

FOREIGN PATENT DOCUMENTS

| | | |
|---|---|---|
| 0097288 | 1/1984 | European Pat. Off. . |
| 2042128 | 9/1980 | United Kingdom . |

*Primary Examiner*—Robert P. Swiatek
*Assistant Examiner*—Cindy A. Cherichetti
*Attorney, Agent, or Firm*—Polster, Lieder, Woodruff & Lucchesi

[57] ABSTRACT

A control unit for an air-polisher is provided, wherein a bleed air line and an air/abrasive line both communicate with a diaphragm valve which in turn communicates with an air polisher handpiece which is stored in a bracket or other holder. The diaphragm valve is closed when the handpiece is in an idle mode and not in its bracket. This blocks pressurized container air and bleed air from carrying water and abrasive out of the nozzle immediately after the handpiece is deactivated, without allowing soluble abrasive within the handpiece to form a plug therein.

38 Claims, 5 Drawing Sheets

CONTROL FOR DENTAL AIR-POLISHER

BACKGROUND OF THE INVENTION

This invention relates to dental air-polishers which clean by abrading teeth with a soluble abrasive and, in particular, to a control for controlling air flow to an air-polisher handpiece when the polisher is deactivated.

In my co-pending application, Ser. No. 477,609, filed Feb. 9, 1990, I disclosed a control unit for controlling both a scaler and an air-polisher. I have found that when the air polisher is deactivated, such as by the operator's removing his foot from a foot switch which is commonly used to operate dental equipment, some air from the pressurized container of abrasive, together with bleed air, continues to flow through to the air polisher tip. When the unit is operating, the water, which is pressurized, causes the water tubing to expand slightly. When the unit is deactivated, the tubing relaxes, squeezing a small amount of water into the handpiece where it is picked up by the residual air flowing through the handpiece and carried out of the handpiece. This may cause liquid to leak or spritz out of the tip and onto the patient, chair, or whatever is below the handpiece at the time. The spritz that is caused may last up to three or four seconds.

In prior art cleaners, pinch valves have been used to control air flow to the tip. For example, U.S. Pat. No. 3,882,638 to Black uses a pinch valve which cuts off all air flow to the handpiece when the handpiece is not in use. However, the use of a pinch valve is undesirable because, after a while, it creates a set in the abrasive tube which leads to the air-polisher. The set causes a permanent constriction in the tube, and it may even close the tube completely. The reason for the resulting set may be seen in FIG. 4 of European application EP 0,097,288 to Mabille, published Jan. 4, 1984. To avoid this set in the tubing, operators are instructed to move the abrasive tube periodically with respect to the pinch valve.

Some prior art cleaners do not depressurize the abrasive containers prior to closing the valve in the line that leads to the air-polisher handpiece. Examples of such prior art cleaners are the above-noted patents to Black and Mabille. In both of these examples it appears that air is delivered to the container when the pinch valves are closed, except of course, when the units are deactivated. Such a configuration requires that the pinch valve work against the full pressure of the abrasive container.

Further, because the Black patent shuts off all air flow to the handpiece, abrasive and water will remain in the handpiece when it is not in use. As was discussed briefly in my co-pending, co-assigned application U.S. Ser. No. 477,748, filed Feb. 9, 1990, if there is not a continuous supply of air to the tip of the handpiece, remaining abrasive may dry in the tip and clog it. Bleed air is needed to blow the abrasive out of the tip, thereby preventing the tip from clogging.

SUMMARY OF THE INVENTION

One object of the present invention is to provide an improved air polisher control unit which will prevent it from dripping or spritzing when deactivated.

Another object is to provide such a control unit which will not allow abrasive to cake up and plug the air-polisher handpiece.

Another object is to provide such a control unit which is resistant to wear and requires little maintenance.

Other objects of this invention will be apparent to those skilled in the art in light of the following description and accompanying drawings.

In accordance with the invention, generally stated, there is provided a dental cleaner which cleans by abrading a tooth with a mild soluble abrasive carried by a gas in the presence of a liquid. The cleaner includes a control unit with a remote handpiece and multi-position switch means for switching the handpiece between a run mode, a rinse mode and an idle mode. The control unit includes a source of pressurized gas in communication with a container of soluble abrasive through a first conduit means, the container of soluble abrasive being in communication with the handpiece through a second conduit means. A diaphragm valve is placed in the second conduit means to shut off air flow to the handpiece without creating a set in the air tubing. A source of control air and means for controlling the control air are provided to control opening and closing of the diaphragm valve. The diaphragm valve includes a flexible resilient diaphragm which is composed of a material resistant to abrasive particles.

The diaphragm valve control-air control means comprises valve means controlled by the multi-position switch means and holding means on the control unit for holding the handpiece. The holding means include sensing means for sensing when the handpiece is in the holding means. The diaphragm valve control means closes the diaphragm valve when the handpiece sensing means senses that the handpiece is not in the holding means and the multi-position switch means has switched the handpiece to the idle mode. In one embodiment, the diaphragm valve control means further closes the diaphragm valve when the multi-position switch means has switched the handpiece to rinse mode. The valve means preferably selectively directs the gas to the container or the diaphragm valve. In one embodiment, full line pressure is used to close the diaphragm valve.

The control unit further includes a source of bleed air which communicates with the second conduit. The bleed air flows to the second conduit means only during the rinse mode.

The control unit further includes mean for at least partially depressurizing the abrasive container. The depressurization means depressurizes the container prior to closing the diaphragm valve. It includes the valve means which is placed in the first conduit means, means for switching the valve means between an open position in which the gas flows to the container of soluble abrasive and a closed position in which the gas is prevented from flowing to the container of soluble abrasive, and valve control means for selectively opening and closing the diaphragm valve. The valve control means does not close the diaphragm valve until after the switching means closes the valve means in the first conduit means, so that the container is depressurized through the second conduit means before the second conduit means valve is closed.

The diaphragm valve includes a control port communicating with the source of control air. The valve means in the first conduit means comprises a first valve and a second valve, each of which have an open port and a normally closed port. In one embodiment, the source of pressurized air is connected to the open port of the first valve and the normally closed port of the second valve.

The normally closed port of the first valve communicates with the container of soluble abrasive and the open port of the second valve communicates with the control air port of the diaphragm valve, wherein the switching means does not open the normally closed port of the second valve until after it closes the normally closed port of the first valve.

In another embodiment, the first valve of the valve means has an inlet which communicates with the source of pressurized air, a normally closed outlet in communication with the container of soluble abrasive, and a normally open output. The second valve has a normally open inlet in communication with the normally open outlet of the first valve and an open outlet in communication with the diaphragm valve control port. In this embodiment, the control means does not open the second valve's normally open inlet until after it opens the first valve's normally closed outlet.

The control unit may also include means for continuing depressurization of the abrasive container after the diaphragm valve. The continuing depressurization means comprises a bleed vent in the container. When the second conduit means is closed by the diaphragm valve, the bleed vent slowly depressurizes the container.

The depressurizing means may also be associated with the abrasive container to depressurize the container after the diaphragm valve is closed. This depressurizing means comprises valve means which places the container in communication with atmosphere through a cap of the container. The valve means includes a push button slidably received in a bore in the cap which is in communication with the interior of the container. The push button includes a head which protrudes from the cap and a flange below the head. The head and the cap define an annular space which is selectively closed by the flange. The push button is biased so as to close the annular space. The push button valve is preferably in communication with the first conduit means.

Another improvement includes means for preventing clogging of the handpiece with soluble abrasive. The clog preventing means includes a source of bleed air in communication with the conduit. The bleed air flows through the valve to the handpiece when the handpiece is in the holding means, and when the handpiece is out of the bracket and in rinse mode. The clog preventing means preferably allows the bleed air to pass through the handpiece during the rinse mode. The source of bleed air communicates with the second conduit between the valve and the handpiece, the valve being closed when the handpiece is in the rinse mode or the idle mode.

A method of using the control unit briefly described above to prevent water from dripping on a patient, chair or the like is also disclosed.

Another improvement to the control unit includes a check valve in the second conduit means. The check valve preferably includes a split manifold having two air paths which communicate with each other by means of the check valve. The split manifold check valve has at least two ports, one port being in communication with the handpiece, a second port being in communication with the second conduit means. The manifold further includes a third port which may communicate with by-pass means for controlling the amount of abrasive the gas entrains. The third port may altenatively be in communication with a source of bleed air. The manifold may also include a fourth port which is communication with container exhausting means for exhausting the container.

The control unit also preferably includes means for controlling the amount of abrasive delivered to the handpiece. The abrasive controlling means includes a shunt line in communication with the first conduit means and the container of abrasive, and means in the container to prevent the shunt line air from disturbing the abrasive in the container. The abrasive disturbing preventing means comprises a downwardly facing deflector spaced from the top of the container so as to form a channel therewith. The shunt air is preferably directed into the channel.

A cover for the container preferably includes a first air path therethrough allowing a source of pressurized air to communicate with the interior of the container, a second air path therethrough for allowing the interior to communicate with an air polisher handpiece, and means for manually depressurizing the container. The depressurizing means comprises valve means which places the container in communication with atmosphere through the container's cover. The valve means comprises a push button slidably received in a bore in the cover which is in communication with the interior of the container. The push button includes a head which protrudes from the cover and a flange within the bore. The head and cover preferably define an annular space which is selectively closed by the flange. The push button is biased so as to close the spacing. The valve is preferably in communication with the first conduit means.

DESCRIPTION OF THE PREFERRED EMBODIMENT

Figure 1:
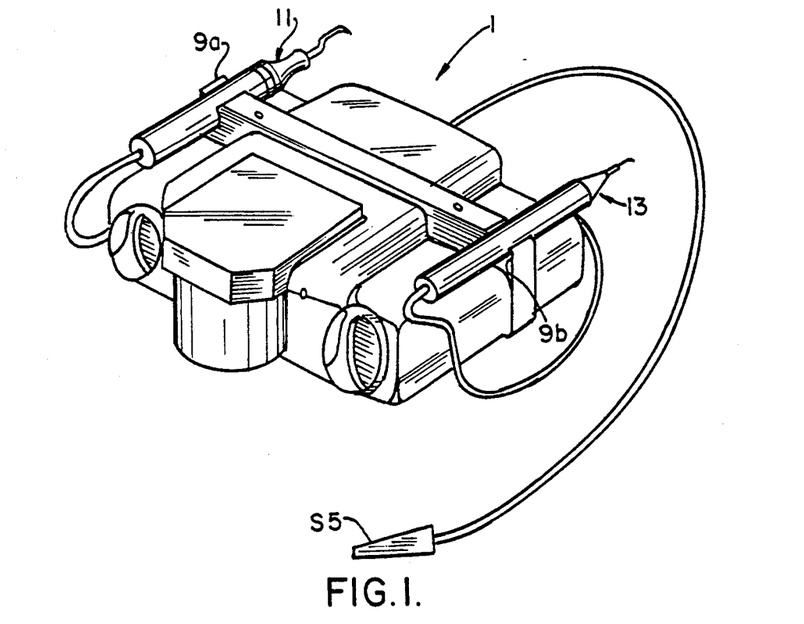
FIG. 1 is a perspective view of a control unit of the present invention.

Referring now to FIG. 1, reference numeral 1 indicates a control unit of the present invention having a scaler handpiece 11, an air-polisher handpiece 13, and brackets 9a and 9b in which the scaler and air-polisher, respectively, are placed when not in use. Brackets 9a and 9b include switches which detect whether or not the handpiece is in the bracket. It will be understood that the nature of the brackets 9a and 9b is not essential to the invention, and the term "bracket" is used broadly herein. The control of the flow of water, air, and electricity by the switches in cooperation with a multi-position foot pedal S5 is fully disclosed in my co-pending application, U.S. Ser. No. 477,609, filed Feb. 9, 1990, which is incorporated herein by reference and is briefly set forth below, identical numbering being used for corresponding parts of the present control. Multi-position foot pedal S5 switches a selected handpiece between idle, rinse, and run modes.

Figure 2:
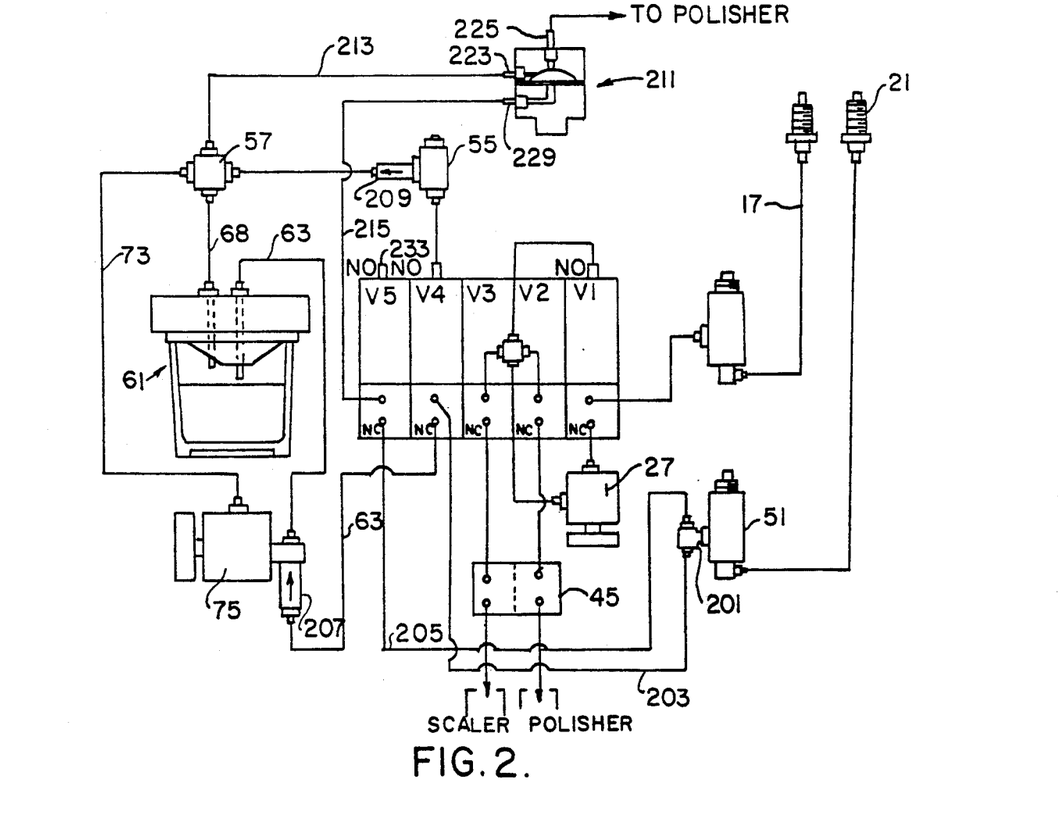
FIG. 2 is a hydraulic/pneumatic schematic of the control unit of FIG. 1.

The flow of water from its source 17 through manual control 27, valves $V_1$-$V_3$ and heater 45 to either the scaler handpiece 11, or the polisher handpiece 13 is the same as in my application Ser. No. 477,609.

The flow of air, however, is slightly different. Pressurized air (approximately 30 psi) enters control unit 1 through a bushing 21 and flows directly to a pressure regulator 51. The air exits regulator 51 through a manifold 201 which directs the air to an open port of valve $V_4$ along line 203 and to the normally closed port of valve $V_5$ along line 205.

As was discussed in my aforementioned application, from valve $V_4$, the air flows either to a manifold 57 as bleed air through a normally open port (designated as NO) of valve $V_4$ when valve $V_4$ is deactivated or to an air/abrasive control valve 75 through the normally closed port (designated as NC) of valve $V_4$ when valve $V_4$ is activated. When valve $V_4$ is activated, upon exiting control valve 75, a portion of the air flows through a shunt line 73 directly to manifold 57. The remaining air flows through line 63 to an abrasive container assembly 61 where the air picks up soluble abrasive and delivers it to manifold 57 via line 68. Air/abrasive control valve 75 and abrasive container assembly 61 are preferably the same as those disclosed in my aforementioned application. However, before entering control valve 75, the air passes through a check valve 207. When valve $V_4$ is deactivated, the bleed air from valve $V_4$ similarly passes through a check valve 209 after passing through a bleed valve 55.

Whether the air exits valve $V_4$ through the normally open port or normally closed port depends upon whether the polisher or scaler is selected and the position of a foot pedal switch S5, as was discussed in my co-pending application. Briefly, if the scaler 11 is selected, by lifting it from its bracket 9a, bleed air flows to manifold 57 independent of the position of the foot pedal. If the polisher 13 is selected, by lifting it from its bracket 9b, bleed air flows to manifold 57 when the pedal is not depressed or when the pedal is depressed to its first (rinse) position. If both or neither the polisher and scaler are selected, bleed air flows to manifold 57. Air flows to the abrasive container assembly 61 only when the air-polisher is selected and when the foot pedal is depressed to its second (run) position. The control unit detects which handpieces are in or out of their holding brackets by switches associated with the brackets 9a and 9b.

The air/abrasive flows from manifold 57 to the inlet of a diaphragm valve 211 via a line 213. The air/abrasive flows from the outlet of diaphragm valve 211 to the air-polisher 13. Diaphragm valve 211 is controlled by air flowing from an open port of valve $V_5$ through a control air line 215. The normally open port of the valve $V_5$ is connected to the air inlet manifold 201, and its normally closed port is connected to atmosphere. Thus, the control line 215 is alternatively connected to a source of pressurized air and to atmosphere.

Figures 4, 5:
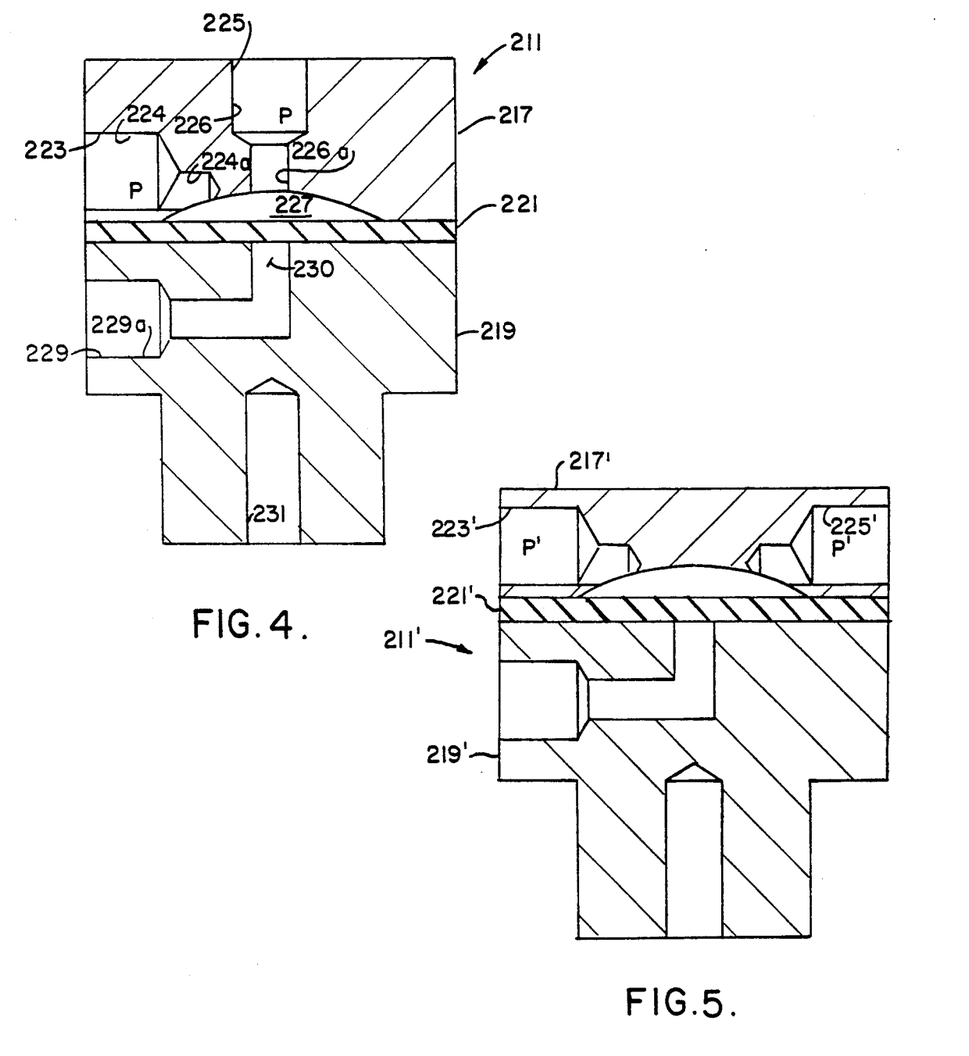
FIG. 4 is a cross-sectional view of one embodiment of a diaphragm valve used in the present invention.
FIG. 5 is a cross-sectional view, corresponding to FIG. 4, of another embodiment of valve.

As seen in FIG. 4, diaphragm valve 211 has a top portion 217 and a bottom portion 219 with a diaphragm 221 positioned therebetween. Top portion 217 has an L-shaped air path P through which the air/abrasive and bleed air flows. An inlet 223 communicates with line 213, and an outlet 225 communicates with polisher 13. The inlet and outlet communicate with each other by way of a chamber 227. Inlet 223 and outlet 225 each include a receiving portion 224 and 226 of sufficient diameter to receive line 213 and the conduit which leads to the handpiece. The tube receiving sections each taper to a section 224a and 226a respectively which leads to chamber 227. Sections 224a and 226a preferably have the same inner diameter as the air/abrasive tubing. Bottom portion 219 includes a control air chamber 230 which communicates with control air line 215 through an inlet 229. Inlet 229 includes a tube receiving section 229a which tapers to the control chamber 230. Chamber 230 preferably is an air path of the same inner diameter as control line 215. Diaphragm 221 rests over the control chamber 230. A bore 231 which receives a mounting screw to mount the valve to the control unit is located at the bottom of bottom portion 219.

The diaphragm 221 is preferably made from a flexible, resilient material, such as a silicone rubber, which resists erosion by the abrasive particles which contact it. The diaphragm also preferably deforms at low pressures (i.e. below approximately 30 psi), so that the same air source may be used for both the control air to the diaphragm valve and the operating air to the polisher. As described hereinafter, the control chamber 230 is pressurized only when the air/abrasive and by-pass air lines have been shut off, so that the pressure in control chamber 230 is adequate to close the diaphragm valve.

When control air passes through line 215, diaphragm 221 is deformed, attaining the shape of cavity 227, to close inlet 223 and outlet 225. When the valve is closed, no air can pass to the handpiece 13. Thus, because the air preferably carries the abrasive particles and water to the teeth, as was discussed in my co-pending application U.S. Ser. No. 477,748, which is incorporated herein by reference, water which is pushed into the handpiece by the relaxing of the water tubing will not be forced through the handpiece. As the water does not have sufficient pressure to exit the handpiece on its own, no water will exit the handpiece when the diaphragm valve is closed. Upon release of the pressure in line 215 (when the normally closed port of valve $V_5$ is closed) diaphragm 221 returns to its original shape, forcing the control air back through line 215 to be vented to the atmosphere through a vent 233, the normally open port of valve $V_5$. Line 215 thus also acts as an exhaust line for the control air.

Figure 3:
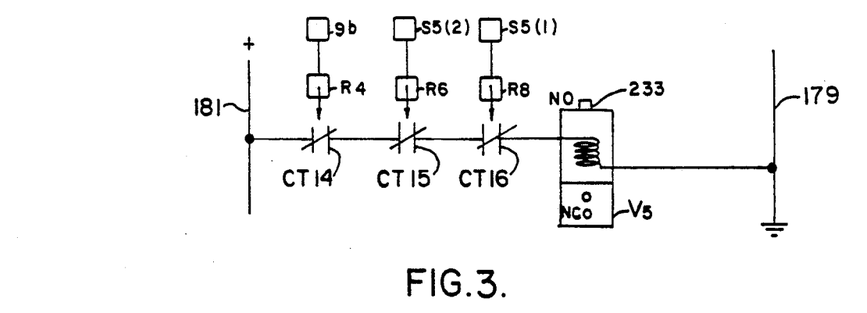
FIG. 3 is an electrical schematic of a control valve which selectively opens and closes a diaphragm valve of the present invention.

As can be seen in FIG. 3, valve $V_5$ is connected in series with three normally closed contacts CT14, CT15, and CT16 between electrical lines 181 and 179 which are indirectly connected to a source of electricity and ground. Contacts CT14, CT15, and CT16 are controlled by relays R4, R6, and R8, respectively. When all of the relays R4, R6, and R8 are de-activated, contacts CT14, CT15, and CT16 are closed and valve $V_5$ is energized. When valve $V_5$ is energized, the normally closed port will open, the vent 233 (its normally open port) will close and control air will flow through the normally closed port of the valve $V_5$ to the diaphragm valve 211, closing it. Conversely, when any one of relays R4, R6, or R8 is activated, one of the contacts CT14, CT15, or CT16 will open, and valve $V_5$ will be de-energized. When valve $V_5$ is de-energized, its vent 233 opens and its normally closed port closes. Thus, air control line 215 is no longer supplied with control air and the diaphragm valve 211 opens, forcing the control air out line 215 and vent 233.

Relays R4, R6, and R8 are selectively activated and deactivated by the opening and closing of the switches associated with brackets 9a and 9b in combination with the foot pedal S5, as is set out in detail in my co-pending application Ser. No. 477,609.

Briefly, when polisher 13 is in its bracket, relay R4 is energized, valve $V_5$ is de-energized, and the diaphragm valve 211 opens to allow bleed air to handpiece 13. This holds true independent of the placement of the scaler handpiece 11, and the position of the foot pedal S5.

When polisher 13 is out of its bracket, there are three possibilities. In a rinse mode, the foot pedal is pressed to its first position; relay R8 is energized, contact CT16 opens, the normally open port of valve $V_4$ opens and bleed air flows through regulator 55 to the polisher. The vent 233 of valve $V_5$ remains open so that diaphragm valve 211 is open.

In a run mode, the foot pedal S5 is pressed to its second position; relay R6 is activated, contact CT15 opens, the normally closed port of valve $V_4$ opens, and air/abrasive flows to the polisher through lines 73 and 68. Again, the vent 233 of valve $V_5$ is open so that diaphragm valve 211 is open.

In an idle mode, the foot pedal is not depressed at all; all the relays R4, R6, and R8 are deactivated, the normally closed port of valve $V_5$ is open to allow air to pass through control line 215 to diaphragm valve 211. Valve 211 is closed and no air passes through to the polisher. Further, the normally closed port of valve $V_4$ is closed and its normally open port is opened. Air flow to power control valve 75, and hence to abrasive container assembly 61 and by-pass line 73 is shut off and the air instead flows through bleed vent 55.

Thus, diaphragm valve 211 is opened unless the polisher is out of its bracket and the foot pedal is not depressed. This will prevent air from flowing through the polisher during the period between the time a technician stops use of the polisher and the point when the polisher is set down in its bracket. During this brief period, water cannot be carried out of the polisher handpiece and the polisher handpiece will not drip or spritz on a patient. However, bleed air is allowed to pass through the polisher when the polisher is placed in its bracket. Thus the abrasive within the polisher will not absorb liquid and plug the polisher while the polisher is not in use and properly placed in its bracket Because the operation of the foot pedal requires the system to go through rinse mode between run mode and idle mode, the air in container assembly 61 and air lines 63, 68, 73, and 213 has a brief moment to escape through the air polisher handpiece 13 prior to closing diaphragm valve 211. Thus, the abrasive container 61 is allowed to at least partially depressurize prior to the closing of diaphragm valve 211, and valve 211 does not have to work against a pressurized airline. This allows for the control air to valve 214 to be at the same pressure as the air to the container assembly 61. In the idle mode, some air will continue to flow through the normally open port of valve $V_4$. This air, however, passes through bleed vent 65 and is minimal. Thus, most of the air is directed to the diaphragm valve control port 229.

FIG. 5 shows a second embodiment of the diaphragm valve. Valve 211' includes a bottom portion 219', a diaphragm 221', and a top portion 217'. Bottom portion 219' and diaphragm 221' are identical to bottom portion 219 and diaphragm 221 of valve 211. Top portion 217' differs from top portion 217 of valve 211 only in that air path P' between inlet 223' and outlet 225' is straight, rather then L-shaped.

Figure 6:
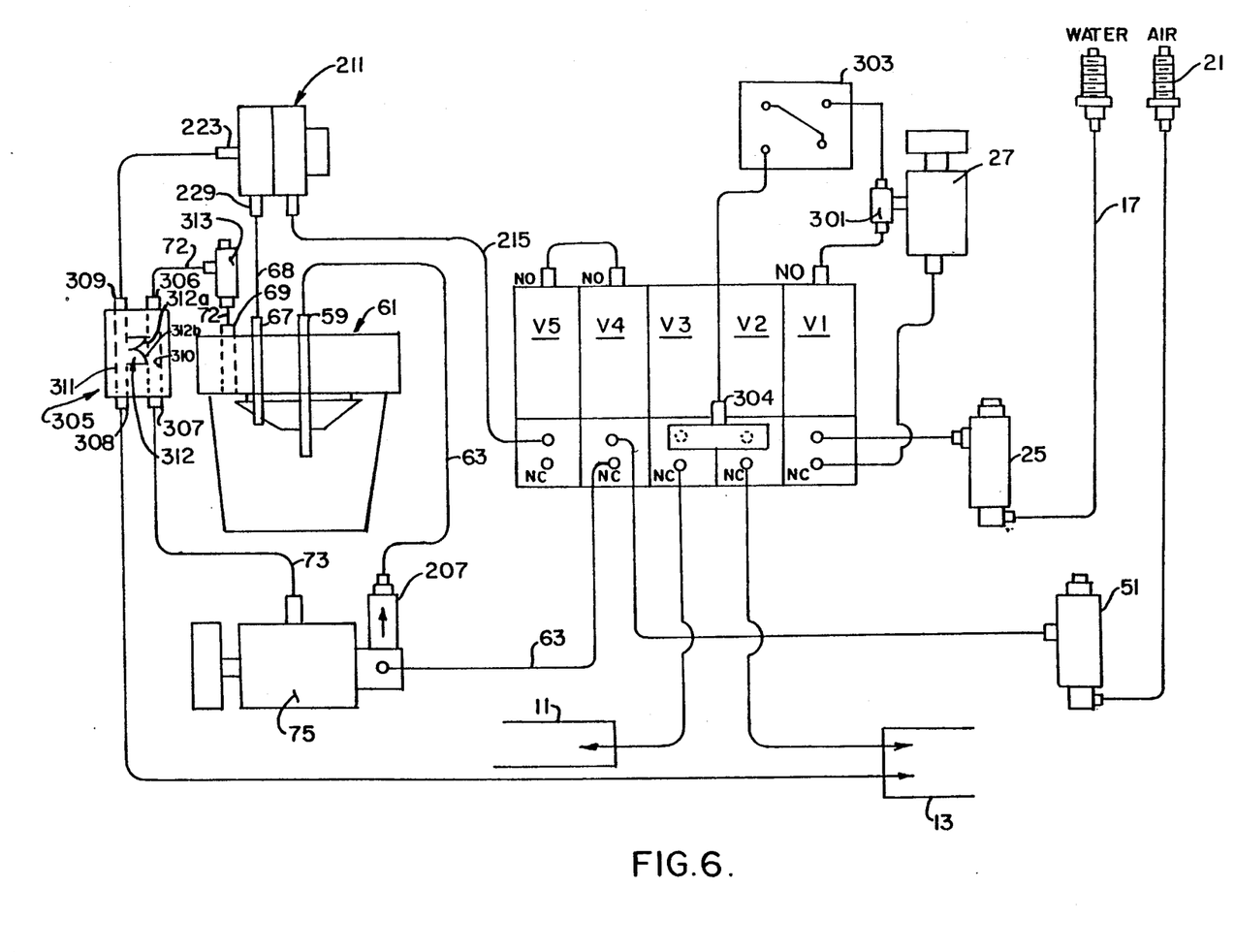
FIG. 6 is a hydraulic/pneumatic schematic of a second embodiment of control unit of the invention.

Turning to FIG. 6, there is shown an alternative pneumatic/hydraulic configuration which has no bleed air. In this configuration, water enters the control unit and flows to a pressure regulator 25 and to the inlet of valve $V_1$. When in the run mode, the water flows from the normally closed port of valve $V_1$ to a water control valve 27. A tee 301 at the exit of control valve 27 directs the water to a double pass water heater 303. Water then flows to a three port manifold 304 which directs the water to valve $V_2$ or $V_3$, depending on whether the scaler 11 or polisher 13 is selected. In the rinse mode, the water flows from the normally open port of valve $V_1$ to tee 301. It by-passes water control valve 27 so that all the water is directed to the selected handpiece.

The air, as before, initially flows to pressure regulator 51. However, all the air then flows to the inlet of valve $V_4$. Depending on the position of foot pedal S5, valve $V_4$ directs the air either to the handpiece 13 or to the diaphragm valve 211 as control air.

When the polisher is in the run mode, valve $V_4$ is activated and the air exits through the normally closed port of valve $V_4$ and is directed to the abrasive control valve 75 which splits the air so that a portion of the air flows through the conduit 63 to abrasive container assembly 61 to pick up abrasive. The remaining air flows through by-pass line 73. Within container assembly 61, the air picks up abrasive, and upon exiting, the air/abrasive flows to diaphragm valve 211 through air line 68.

Diaphragm valve 211 and by-pass line 73 are both connected to a split-manifold 305 having four ports 306≃309 which define two separate air paths 310 and 311. Ports 306 and 307 are in fluid communication with each other through air path 310. Ports 308 and 309 are similarly in fluid communication through air path 311. The air path 310 and the air path 311 are joined by a duck-bill check valve 312, having two resilient flaps 312a and 312b, which prevents air flow from air path 311 to 310 but allows air flow from path 310 to 311. When air passes from path 310 to 311, flaps 312a and 312b separate to allow air to pass. However, when the flow is reversed, the resilient flaps are brought together to prevent flow from path 311 to path 310.

By-pass line 73 is connected to port 307 of manifold 305. Port 306 communicates with an exhaust port 69 of container assembly 61 over an exhaust line 72. Port 308 of manifold 305 communicates with the polisher handpiece 13. Manifold port 309 communicates with outlet 223 of diaphragm valve 211.

A bleed vent 313 is inserted in line 72 to depressurize container assembly 61 upon the discontinuance of air thereto. Bleed vent 313 is a needle valve which is sufficiently closed so it will take approximately one minute for container 61 to reach atmospheric pressure.

In the rinse mode, valve $V_4$ is deactivated and the air is directed out its normally open port. As there is no bleed air in this embodiment, no air is directed to handpiece 13. Thus, there is only water passing through handpiece 13 when in the rinse mode. The normally open port of valve $V_5$ is not opened during rinse mode. Thus, the diaphragm valve 211 is opened and container assembly 61 may depressurize through the diaphragm valve 211.

Check valve 312 operates to prevent water from backing up too far in the air/abrasive line during a rinse. Preferably, it is placed in the handpiece 13. In the event the conduit between bleed vent 313 and manifold 305 is removed, the output of diaphragm valve 211 could be connected to port 306 of the manifold 305. This would prevent water from backing up to the diaphragm valve.

When foot pedal S5 is not depressed (idle mode), valve $V_4$ is deactivated, its normally open port is opened, and the normally open port of valve $V_5$ is opened. The air then flows through the open port of valve $V_5$ to the control chamber 230 of diaphragm valve 211 to close the valve. Thus, as before, when polisher 13 is in an idle mode, control air is directed to diaphragm valve 211.

Valve $V_5$ is controlled so that it is activated and deactivated simultaneously with valve $V_4$. The normally open and normally closed ports of valves $V_4$ and $V_5$ open and close together and valve 211 is closed during both the rinse and idle modes. The diaphragm valve 211 does not have to work against the full pressure of container assembly 61, as it is depressurized through bleed valve 313.

Valve $V_5$, alternatively, could be controlled so that there is a time delay between the opening of the normally open port of valve $V_4$ and the normally open port of valve $V_5$, i.e. valve $V_4$ is deactivated and valve $V_5$ is activated when the polisher is in the rinse mode. This would allow for depressurization of container assembly 61 through diaphragm valve 211. Bleed vent 313 would then allow for continued depressurization of container assembly 61 after closing of the diaphragm valve 211 through manifold air path 310, check valve 312, and polisher handpiece 13. The container assembly 61 would therefore reach atmospheric pressure after approximately one minute.

The embodiment of FIG. 6 eliminates bleed air to the handpiece when the polisher is in rinse mode. The only air that does flow to the handpiece is the air in the container at the time air to container assembly 61 is discontinued. The air that does not escape through handpiece 13 prior to closing diaphragm valve 211 is slowly exhausted through bleed vent 313, check valve 305 and handpiece 13.

All bleed air may be eliminated by removing the line between bleed vent 313 and check valve 305. In this case, port 306 would be blocked. Alternatively, the diaphragm valve outlet 223 could be connected to manifold port 306 and port 309 could be blocked.

Figures 7, 8:
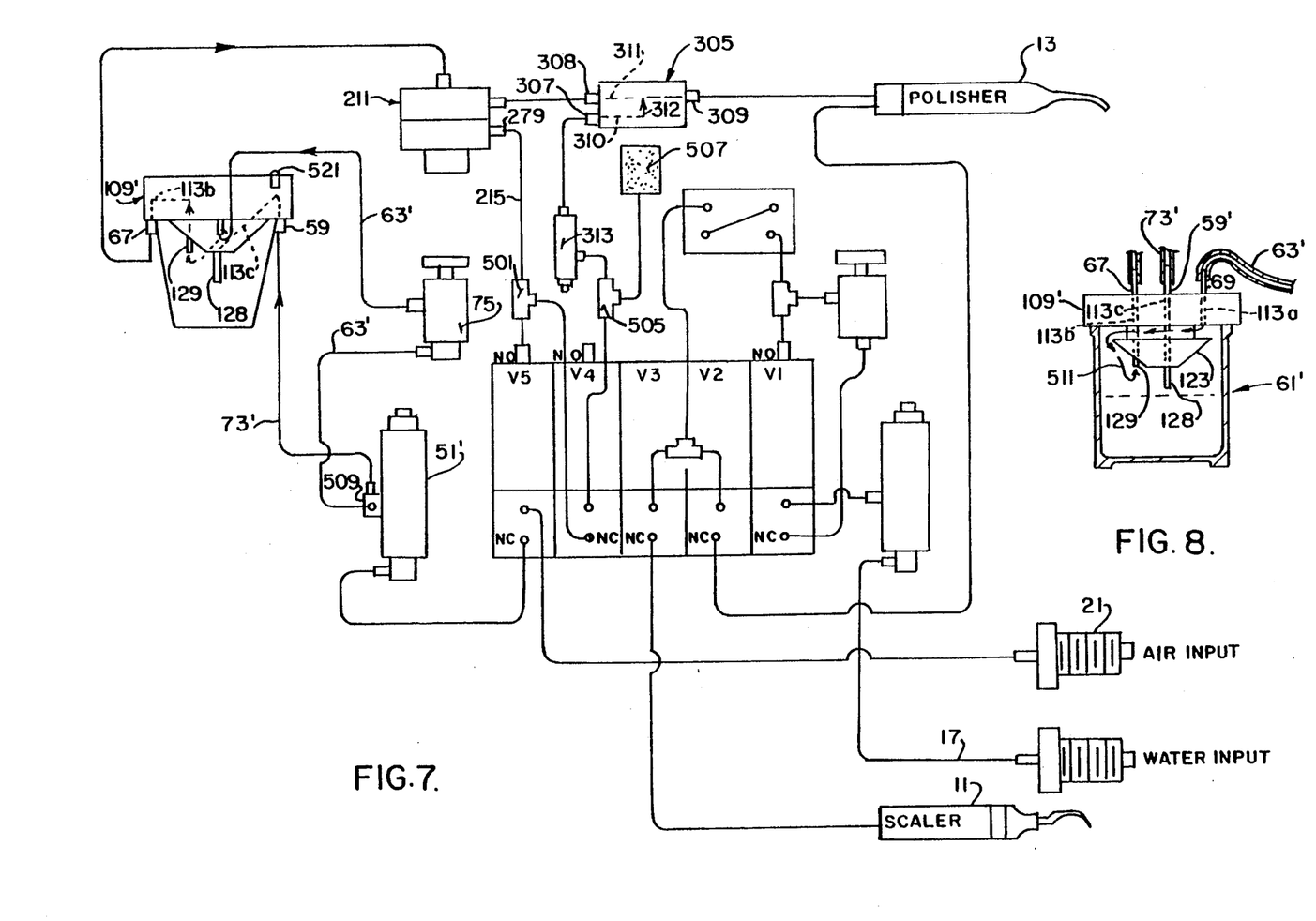
FIG. 7 is a hydraulic/pneumatic schematic of another embodiment of control unit of the invention.
FIG. 8 is a cross-sectional view of an abrasive container assembly.

Turning to FIG. 7, there is shown an alternative pneumatic/hydraulic configuration which allows full line pressure to control the diaphragm valve and shunts the powder control air through the powder container, rather than around it. The liquid flow through this configuration is the same as in FIG. 6 and will not be discussed.

The air flow, however, is different from the configuration of FIGS. 1 or 6. Pressurized air (approximately 65 psi) enters the system through bushing 21 and flows directly to the open port of valve $V_5$. If valve $V_5$ is relaxed or deactivated (run or idle mode), the air exits valve $V_5$ through its normally open port, passes through a "T" fitting 501 and is directed to the control port of diaphragm valve 211. The third port of "T" fitting 501 is connected to the normally closed port of valve $V_4$. Valve $V_4$ is electrically connected to valve $V_2$ and is thus only activated during the run and rinse modes. Thus, when the unit is in idle mode, all air is directed to the diaphragm as control air. When it is in rinse mode, air flows through valve $V_4$ as bleed air, however, as will be explained below, most of the air still flows to the diaphragm valve.

In the rinse mode, valves $V_4$ and $V_2$ are activated to deliver air and water to handpiece 13. Valve $V_5$ remains deactivated. Thus, the air continues to flow through the normally open port of valve $V_5$ to diaphragm valve control port 229. However, some air passes through the third port of "T" fitting 501 and enters valve $V_4$ through its normally closed port, the air exits valve $V_4$ through its open port and enters another "T" fitting 505 which directs the air flow through one outlet to a foam noise muffler 507 and through another outlet to bleed vent 313, which is connected to port 307 of manifold 305. The air enters manifold 305 through path 310 and enters path 31 through the duck billed check valve 312. Because diaphragm 211 is closed, the air is directed to handpiece 13. Bleed vent 313 reduces the pressure of the air entering manifold 305, however, the pressure of the air entering handpiece 13 is sufficient to prevent water from backing up into the air system. Because of the restriction created by bleed vent 313 and muffler 507, most of the air exiting valve $V_5$ is directed to diaphragm valve 211.

When the handpiece 13 is switched to run mode, valves $V_2$ and $V_4$ remain activated and valve $V_5$ is activated, directing the air to container assembly 61' rather than to diaphragm valve 211. Because air is no longer directed to control port 229 of diaphragm valve 211, the diaphragm valve opens. The control air passes into the normally closed port of valve $V_4$ and is vented to atmosphere through muffler 507. Because of the restriction created by bleed vent 303 and muffler 507, most of the control air is vented to the atmosphere. The muffler acts to disperse the air and thereby eliminates a "hiss" which is created by the control air being vented to the atmosphere in the absence of muffler 507.

The air flows from the normally closed port of valve $V_5$ to an air regulator 51, which reduces the air pressure from a line pressure of 65 psi to approximately 30 psi. A three port manifold 509 at the exit of air regulator 51' separates the air into two lines. The air is sent to the abrasive container assembly over line 73' and to a shunt line 63' to regulate the amount of abrasive entrained and delivered to handpiece 13.

The abrasive entraining air from line 73' enters the container assembly through port 59 in cap 109' and velocity tube 128 to fluff up and entrain the abrasive. The air/powder exits through pick-up tube 129 and port 67 of cap 109, and is directed to the diaphragm valve 211. From the diaphragm valve, the air/powder flows through path 311 of manifold 305 to handpiece 13.

It will be noted that the entrance and exit of diaphragm valve 211 are reversed with respect to FIGS. 1 and 6. Referring back to FIG. 4, by making port 225 the inlet, the diaphragm 221 is better able to maintain the valve closed when control air is passed to control chamber 230. This is because the control air is directly counteracting the pressure from the container.

The shunt line is directed to, rather than around, container assembly 61'. Control valve 75 in line 63' controls the flow of shunt air and therefore the amount of abrasive powder entrained. Turning to FIG. 8, the shunt air enters cap 109' through port 69 and air path 113a in cap 109'. Air path 113a is relatively wide in relation to the diameter of velocity tube 128, preferably having an inner diameter of 0.047". Thus the shunt air enters assembly 61' with low velocity and low pressure. The shunt air therefore will not fluff nor add to the fluffing of the abrasive powder and will not affect the amount of abrasive entrained. To further assure that the shunt air will not fluff the abrasive powder, path 113a opens into the container assembly in a groove formed by the inside face of cap 109' and a deflector 123 which is secured to cap 109'. The shunt air follows a path shown by arrows 511 in FIG. 8. As can be seen, it flows around the groove and the surface of deflector 123 to pick up tube 129 where it exits container assembly 61'.

The abrasive container assembly 61' is not provided with an automatic vent to depressurize the container when the polisher is shifted to rinse mode. Keeping the container pressurized throughout a cleaning procedure eliminates the need to repressurize the container every time a hygienist switches from rinse mode to run mode. This provides "instant cleaning", i.e. there is no delay or very little delay between the time the polisher is switched into run mode and the time air/abrasive exits the polisher tip. After the cleaning procedure is finished the container assembly will slowly depressurize, i.e. in about 8-10 minutes.

Because full line pressure is delivered to diaphragm valve 211, there is no need to depressurize container assembly 61' in order to properly close valve 211. As can be seen, full line pressure (65 psi) is delivered to the control air port 229 of diaphragm valve 211. By using full line pressure to control valve 211, prior depressurization of container assembly 61' does not have to be relied on to close valve 211. Further, the greater differences in pressure between the control chamber 230 and air/abrasive line creates a more secure closing of valve 211.

Figure 9:
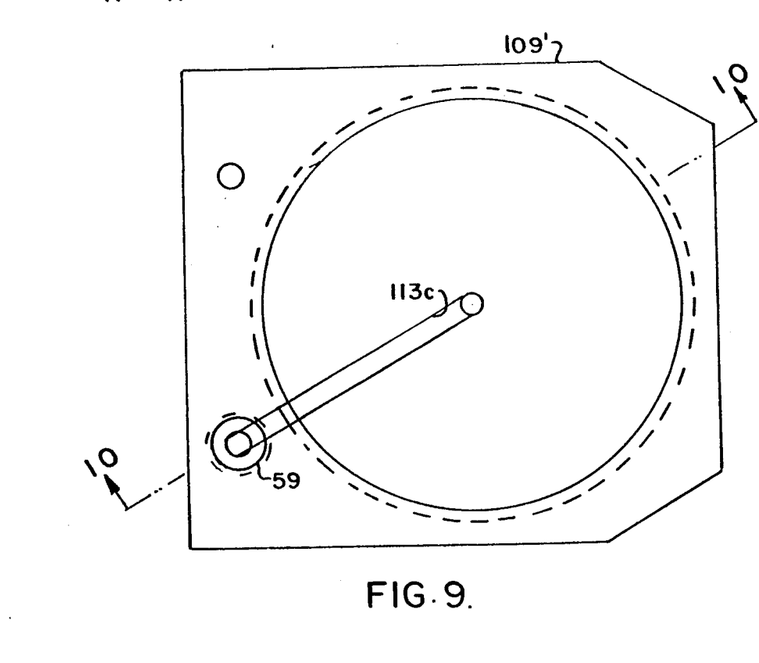
FIG. 9 is a bottom plan view of a cap for the abrasive container assembly of FIG. 8.
Figure 10:
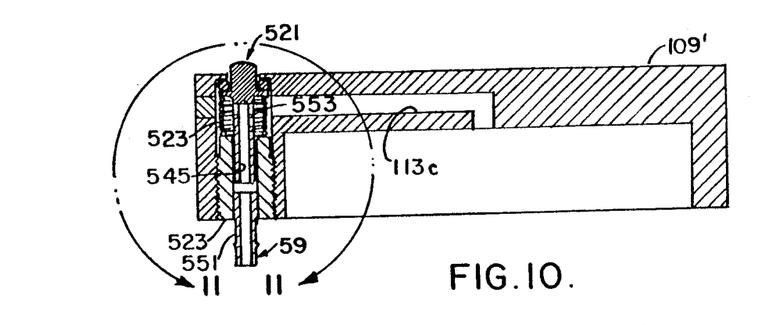
FIG. 10 is a cross-sectional view of the cap along line 10—10 of FIG. 9.
Figure 11:
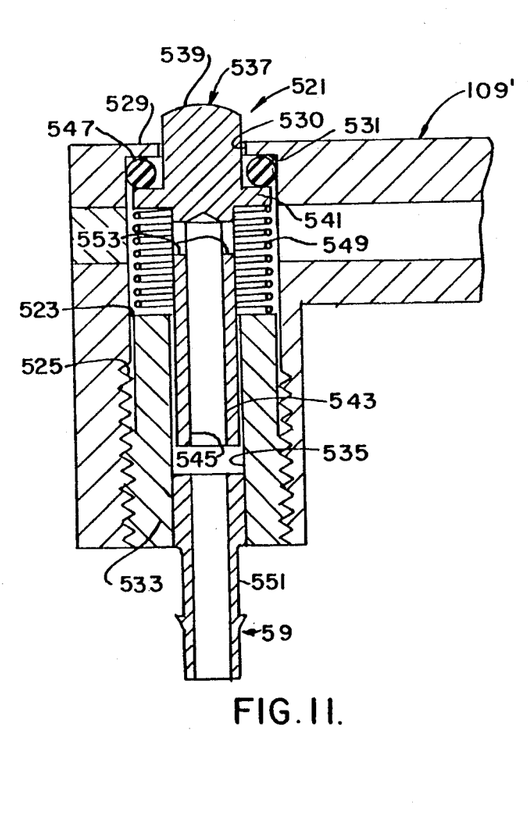
FIG. 11 is an enlarged fragmentary view taken along line 11—11 of FIG. 10.

Turning to FIGS. 9-11, a pressure release valve 521 is provided for quick depressurization of container assembly 61' to enable the hygienist to quickly change jars of abrasive powder.

Cap 109' includes a threaded bore 523 therethrough which communicates with the velocity tube 128 via an air path 113c and which receives pressure release valve 521. Bore 523 is open at both ends. It is threaded at its bottom 525 and partially closed at its top 529 to form a shoulder 531. An externally threaded valve screw 533 is screwed into the bottom of cap bore 532. Valve screw 533 has an aperture 535 therethrough.

A valve button 537 having a head 539, a flange 541, and a leg 543 with a bore 545 therethrough is slidably received in the top of cap bore 523. The diameter of head 539 is preferably about 0.016" smaller then the diameter of the opening 530 formed by shoulder 531, forming an annular opening having an area of about 0.00372 in². Flange 541 is wider than the opening formed by shoulder 531 and head 539 so that it can seal off the opening. An O-ring 547 is placed between flange 541 and shoulder 531 to make the seal air tight. Valve button 537 is biased upwardly to seal opening 530 by a spring 549.

Leg 543 of valve button 537 is slidably received in valve screw aperture 535. A barb 551 is fitted into the bottom of valve screw aperture to form port 59. Barb 551 does not interfere with the sliding movement of valve button 537. Leg 543 has an aperture 553 which crosses bore 545 so that bore 545 and port 59 communicate with air path 113c and velocity tube 128. To depressurize the chamber, push button 537 is depressed. The air within container 61' will flow up velocity tube 128, through path 113c and into cap bore 523. Because flange 541 is smaller in diameter than the diameter of bore 523, the air will flow around the flange 541 and head 539 and out of the assembly.

During operation, valve button 537 is biased upward by spring 549 to close off the opening 530. The air pressure within bore 523 during a cleaning procedure (i.e. in run mode) will further aid in biasing valve button 537 upward to close opening 530.

The flange 541 has a diameter that is approximately 0.022" smaller than the inner diameter of bore 523, forming an annular area between the flange and bore wall of approximately 0.009 in². This is larger than the annular opening formed by head 539 and shoulder 531 and thus does not limit the rate o depressurization.

Pressure release valve 521 may alternatively be aligned with the shunt port 69 and shunt line 63' rather then with port 59 and pick-up air line 73'. This eliminates the possibility of abrasive being pulled through release valve 521 during depressurization by placing the air exit through shunt path 113a rather then through velocity tube 128.

Numerous variations, within the scope of the appended claims, will be apparent to those skilled in the art in light of the forgoing disclosure and accompanying drawings.

Having thus described the invention, what is claimed and desired to be secured by Letters Patents is:

1. In a dental cleaner which cleans by abrading a tooth with a mild soluble abrasive carried by a gas in the presence of a liquid, the cleaner comprising a control unit and a remote handpiece, and multi-position switch means for switching said handpiece between a run mode, a rinse mode and an idle mode; the control unit comprising a source of pressurized gas in communication with a container of soluble abrasive through a first conduit means, said container of soluble abrasive being in communication with said handpiece through a second conduit means; the improvement comprising a diaphragm valve in said second conduit means, said diaphragm valve having an air path therethrough, a flexible resilient diaphragm located in said air path to selectively open and close said air path; a source of control air for controlling said diaphragm valve, and means for controlling said control air and hence said diaphragm valve.

2. The improvement of claim 1, wherein said diaphragm is composed of a material resistant to abrasive particles, said diaphragm valve including a control chamber portion in communication with said source of control air and an air passage chamber having an inlet and an outlet, said diaphragm separating said control chamber from said air passage chamber and covering at least one of said inlet and said outlet when said pressure chamber is pressurized.

3. The improvement of claim 1, wherein said diaphragm valve control-air control means comprises valve means controlled by said multi-position switch means and holding means on said control unit for holding said handpiece, said holding means having electrical sensing means for sensing when said handpiece is in said holding means; wherein said diaphragm valve control means closes said diaphragm valve when said handpiece sensing means senses said handpiece is not in said holding means and said multi-position switch means has switched said handpiece to said idle mode.

4. The improvement of claim 3, wherein said diaphragm valve control means further closes said diaphragm valve when said multi-position switch means has switched said handpiece to rinse mode.

5. The improvement of claim 4 wherein said valve means selectively directs said gas to said container or said diaphragm valve.

6. The improvement of 5, wherein full line pressure is used to close said diaphragm valve.

7. The improvement of claim 1, wherein said control unit further includes a source of bleed air, said bleed air communicating with said second conduit.

8. The improvement of claim 7, wherein said bleed air flows to said second conduit means only during said rinse mode.

9. The improvement of claim 1 further including means for at least partially depressurizing said abrasive container.

10. The improvement of claim 9, wherein said depressurization means depressurizes said container prior to closing said diaphragm valve, said depressurization means comprising valve means in said first conduit means, means for switching said valve means between an open position in which said gas flows to said container of soluble abrasive and a closed position in which said gas is prevented from flowing to said container of soluble abrasive, and valve control means for selectively opening and closing said diaphragm valve, wherein said valve control means does not close said diaphragm valve until after said switching means closes said valve means in said first conduit means, whereby said container is depressurized through said second conduit means before said diaphragm valve is closed.

11. The improvement of claim 10, wherein said diaphragm valve includes a control port communicating with a source of control air.

12. The improvement of claim 11, wherein said valve means in said first conduit means comprises a first valve and a second valve, each said valve having an open port and a normally closed port, said source of pressurized air being connected to said open port of said first valve and said normally closed port of said second valve, said normally closed port of said first valve communicating with said container of soluble abrasive, said open port of said second valve communicating with said control air port of said diaphragm valve, wherein said switching means does not open said normally closed port of said second valve until after it closes said normally closed port of said first valve.

13. The improvement of claim 11, wherein said valve means in said first conduit means comprises a first valve and a second valve, said first valve having an inlet communicating with said source of pressurized air, a normally closed outlet in communication with said container of soluble abrasive, and a normally open output; said second valve having a normally open inlet in communication with said normally open outlet of said first valve and an open outlet in communication with said diaphragm valve control port.

14. The improvement of claim 13, wherein said control means does not open said second valve's normally open inlet until after it opens said first valve's normally closed outlet.

15. The improvement of claim 9, said improvement further including means for continuing depressurization of said abrasive container after said diaphragm valve is closed.

16. The improvement of claim 15, wherein said continuing depressurization means comprises a bleed vent in said container.

17. The improvement of claim 16, wherein when said second conduit means is closed, said bleed vent slowly depressurizes said container.

18. The improvement of claim 9 further including means for depressurizing said abrasive container after said diaphragm valve is closed; said depressurizing means comprising valve means which places said container in communication with atmosphere through a cap of said container.

19. The improvement of claim 18 wherein said valve means comprises a push button slidably received in a bore in said cap; said bore being in communication with the interior of said container, said push button including a head which protrudes from said cap and a flange below said head; said head and said cap defining an annular space which is selectively closed by said flange, said push button being biased so as to close said annular space.

20. The improvement of claim 19 wherein said valve is in communication with said first conduit means.

21. A control system for preventing liquid from exiting a dental air-polisher handpiece when said handpiece is deactivated; said air polisher comprising handpiece holding means having electrical means for sensing if said handpiece is in said holding means, a control unit including a source of liquid in communication with said handpiece, a source of gas in communication with a source of soluble abrasive, said source of soluble abrasive being in communication with said handpiece via a conduit, a valve in said conduit, said valve having an air path therethrough; means for switching said handpiece between an idle mode, a run mode, and a rinse mode, and electrical control means responsive to said switching means and said sensing means for maintaining said valve closed both when said handpiece is in said holding means and when said handpiece is in an idle mode and not in said holding means.

22. The control system of claim 21, wherein said valve control means further closes said valve when said switching means has switched said handpiece to rinse mode.

23. The control system of claim 22, wherein full line pressure is used to close said valve.

24. The control system of claim 21, wherein said control system further includes means for preventing clogging of said handpiece by soluble abrasive, said clog preventing means comprising a source of bleed air in communication with said conduit.

25. The control system of claim 24, wherein said bleed air is connected to flow through said valve to said handpiece when said handpiece is in said holding means, and when said handpiece is out of said bracket and in rinse mode.

26. The control system of claim 24 wherein said clog preventing means allows said bleed air to pass through said handpiece during said rinse mode.

27. The control system of claim 26 wherein said source of bleed air communicates with said conduit between said valve and said handpiece, said valve being closed when said handpiece is in said rinse mode or said idle mode.

28. The control system of claim 21, wherein said valve is a diaphragm valve.

29. In an air-polisher system, a method for preventing water from dripping on a patient, chair, or the like when a polisher handpiece is de-activated; said air-polisher system comprising a source of liquid in communication with an air-polisher handpiece, a source of pressurized gas, a container of soluble abrasive which communicates with said source of gas by a first conduit means and with said air-polisher handpiece via a second conduit means, a valve in said second conduit means, a source of bleed air in communication with said second conduit behind said valve, means for switching said polisher between a run mode, a rinse mode, and an idle mode; means for determining whether said polisher is in a run mode, a rinse mode, or an idle mode, and holding means for storing said handpiece having handpiece sensing means for sensing whether said handpiece is in or out of said holding means; said method comprising:

detecting if said handpiece is in said holding means;

detecting if said polisher is in a run, rinse, or idle mode;

closing said valve if it is detected that said handpiece is not in its bracket and that said polisher is in idle mode; and opening said valve if it is detected that said handpiece is in its holding means.

30. The method of claim 29 further including as step of closing said valve when said determining means determines said polisher is in a rinse mode.

31. The method of claim 29, said method further including a step of allowing bleed air to flow through said handpiece when said sensing means senses said handpiece to be in said holding means.

32. A dental cleaner which cleans by abrading a tooth with a mild soluble abrasive carried by a gas in the presence of a liquid, the cleaner comprising a control unit and a remote handpiece, the control unit comprising a source of pressurized water in communication with said handpiece and a source of pressurized air in communication with a first valve means having a first port and a second port; said first port being in communication with a container of soluble abrasive over a first conduit means, said container being in communication with said handpiece over a second conduit means; a diaphragm valve including an air path, a diaphragm in said air path, and a control port, said second port being in communication with said control port via a third conduit means, and means to alternatively selectively direct said air to one of said container and said diaphragm valve control port so that full line pressure is directed to said control port.

33. The dental cleaner of claim 32 further including a source of bleed air said source of bleed air being in communication with said second conduit means via a fourth conduit means, said fourth conduit means being in communication with said third conduit means.

34. The dental cleaner of claim 32 further including second valve means in said fourth conduit means and means for controlling said second valve means so that bleed air flows to said second conduit means only during said rinse mode.

35. The dental cleaner of claim 34 including means for exhausting said control air when said diaphragm valve is relaxed, said exhausting means including said second valve means.

36. The dental cleaner of claim 35 wherein said second valve means is in communication with means for silencing the exhausting of said control air, said silencing means comprising a foam muffler.

37. The dental cleaner of claim 32 further including means for controlling the amount of abrasive delivered to said handpiece, comprising a shunt line in communication with said first conduit means and said container of abrasive, and means in said container to prevent said shunt line air from disturbing said abrasive in said container.

38. The dental cleaner of claim 37 wherein said means comprises a downwardly facing deflector spaced from the top of said container so as to form a channel therewith, said shunt air being directed into said channel.

* * * * *